United States Patent
Guyre et al.

(10) Patent No.: US 7,144,710 B2
(45) Date of Patent: Dec. 5, 2006

(54) METHOD FOR DETECTING INFLAMMATION AND INFLAMMATORY CONDITIONS

(75) Inventors: Paul M. Guyre, Hanover, NH (US); Peter M. Morganelli, Sharon, VT (US); Nicholas J. Goulding, Harpenden (GB)

(73) Assignee: Trustees of Dartmouth College, Hanover, NH (US)

( * ) Notice: Subject to any disclaimer, the term of this patent is extended or adjusted under 35 U.S.C. 154(b) by 645 days.

(21) Appl. No.: 10/240,382

(22) PCT Filed: Mar. 27, 2001

(86) PCT No.: PCT/US01/09577

§ 371 (c)(1),
(2), (4) Date: Apr. 17, 2003

(87) PCT Pub. No.: WO01/73435

PCT Pub. Date: Oct. 4, 2001

(65) Prior Publication Data

US 2003/0215885 A1    Nov. 20, 2003

Related U.S. Application Data

(60) Provisional application No. 60/192,529, filed on Mar. 28, 2000.

(51) Int. Cl.
*G01N 33/543* (2006.01)

(52) U.S. Cl. .................. 435/7.94; 435/7.1; 435/7.2; 435/7.92; 435/372; 435/518; 435/523; 435/536; 435/538; 435/546; 435/548; 435/63

(58) Field of Classification Search .......... 435/7.1, 435/7.2, 7.92, 7.93, 7.94, 7.95, 372; 436/517, 436/518, 523, 547, 548, 63, 66, 536, 538, 436/546
See application file for complete search history.

(56) References Cited

OTHER PUBLICATIONS

Coligan et al. (Current Protocols in Immunology, Greene Publishing Associates and Wiley-Interscience, New York, 1991., pp. 2.1.1-2.1.3. 2.1.9-2.1.11, and 2.1.17-2.1.22).*
Droste et al., Shedding of CD163, a Novel Regulatory Mechanism for a Member of the Scavenger Receptor Cysteine-Rich Family, Biochemical and Biophysical Research Communications 23: 110-113 (1999).*
Blaschitz et al., "Antibody Reaction Patterns in First Trimester Placenta:Implications for Trophoblast isolation and Purity Screening", Placenta 2000 21:733-741.
Hintz et al., "Glucorticoids and LPS Synergistically Increase Expression of CD163 on Cultured Human Monocytes", FASEB J. 2000 14 (6) :Supp. (S) , A1143, Abstract No. 148.25.
Högger et al., "Identification of the Integral Membrane Protein RM3/1 on Human Monocytes as a Glucocorticoid-Inducible Member of the Scavenger Receptor Cysteine-Rich Family (CD163)[1]", J. Immunology 1998 161 (4) :1883-1890.
Van Den Heuvel et al., "Regulation of CD163 on Human Macrophages:Cross-linking of CD13 Induces Signaling and Activation", J. Leukocyte Biol. 1999 66(5) :858-866.
Sulahian et al., "Human Monocytes Express CD163, Which is Upregulated by IL-10 and Identical To p. 155", Cytokine 2000 12(9) :1312-1321.
Droste et al., "Shedding of CD163, a Novel Regulatory Mechanism for a Member of the Scavenger Receptor Cysteine-Rich Family", Biochemical and Biophysical Research Communications 1999 256:110-113 XP-002296648.
Ritter et al., "The Scavenger Receptor CD163 :Regulation, Promoter Structure and Genomic Organization", Pathobilogy 1999 67:257-261 XP009036479.
Sulahian et al., "Development of an ELISA to measure soluble CD163 in biological fluids", Journal of Immunological Methods 2001 252:25-31 XP-002296647.

* cited by examiner

*Primary Examiner*—Gailene R. Gabel
(74) *Attorney, Agent, or Firm*—Licata & Tyrrell P.C.

(57) ABSTRACT

Methods for detecting the inflammatory biomarkers molecule CD 163 in biological samples are provided. Also provided are methods for monitoring the course of an inflammatory process or condition in a patient and compositions and methods for preventing and treating inflammation and inflammatory processes.

2 Claims, No Drawings

METHOD FOR DETECTING INFLAMMATION AND INFLAMMATORY CONDITIONS

This application claims benefit of priority from PCT/US01/09577, filed Mar. 27, 2001 and U.S. Provisional Patent Application Ser. No. 60/192,529, filed Mar. 28, 2000.

INTRODUCTION

This invention was supported in part by funds from the U.S. government (NIH Grant No. AI4086) and the U.S. government may therefore have certain rights in the invention.

BACKGROUND OF THE INVENTION

Mononuclear phagocytes (monocytes and macrophages) are critical components of both innate and acquired immunity and are found in virtually every tissue of the body, including the central nervous system. Mononuclear phagocytes participate in both antibody dependent and independent cytotoxicity, phagocytosis and killing of bacteria, destruction of effete erythrocytes, presentation of antigens for T cell activation, and secretion of a wide variety of inflammatory cytokines.

The secretion of inflammatory cytokines, as well as mononuclear phagocyte effector functions, are greatly influenced by soluble mediators. For example, priming by interferon gamma (IFNγ) and exposure to lipopolysaccharide, tumor necrosis factor alpha (TNFα), interleukin-1 (IL-1), or granulocyte-macrophage colony stimulating factor (GM-CSF) can stimulate mononuclear phagocytes to secrete inflammatory cytokines such as TNFα, IL-1 and interleukin-6 (IL-6) (Auger, M. J. and J. A. Ross. 1992. In: *The Macrophage: the natural Immune System*, New York: Oxford University Press, pp. 1-74). Interleulkin-10 (IL-10; originally knows as cytokine synthession inhibitory factor) has been shown to inhibit the expression of a wide range of inflammatory cytokines in vitro (Berkman, N. et al. 1995. *J. Immunol*. 155:4412–4418; de Waal Malefyt, R. et al. 1991. *J. Exp. Med.* 174:1209–1220) as well as in vivo (Chernoff, A. E. et al. 1995. *J. Immunol.* 154:5492–5499; van der Poll, T. et al. 1997. *J. Immunol.* 158:1971–1975). Glucocorticoids, interleukin-4 (IL—4) and interleukin-13 (IL13) have also been shown to down regulate the expression of inflammatory cytokines produced by mononuclear phagocytes. In addition to inhibiting the release of inflammatory cytokines, glucocorticoids have also been shown to upregulate the expression of CD163 on mononuclear phagocytes (Hogger, P. et al. 1998. *Pharm. Res*. 15:296–302; Hogger, P. et al. 1998. *J. Immunol*. 161:1883–1890; Wenzel, I. et al. 1996. *Eur. J. Immunol*. 26:2758–2763).

CD163 is a mononuclear phagocyte restricted antigen which is a member of the cysteine rich scavenger receptor family group B. Normal human macrophages stain brightly for CD163 and glucocorticoid treatment in vivo increases CD163 expression (Zwadlo-Klarwasser, G. et al. 1992. *Int. Arch. Allergy Immunol*. 97:178–180; Zwadlo-Klarwasser, G. et al. 1990. *Int. Arch. Allergy Immunol*. 91:175–180). It has been suggested that these CD163 bright macrophages may play a role in the resolution of inflammation as they are found in high numbers in inflamed tissues (Zwadlo, G. et al. 1987. *Exp. Cell Biol*. 55:295–304) and have been shown to release an incompletely characterized anti-inflammatory mediator (Zwadlo-Klarwasser, G. et al. 1995. *Int. Arch. Allergy Immunol.* 107:430–431).

One mononuclear phagocyte marker that bears a striking resemblance to CD163 is p155 (Morganelli, P. et al. 1988. *J. Immunol.* 140:2296–2304). Expression of this 134 kDa (non-reduced)/155 kDa (reduced) glycoprotein is restricted to mononuclear phagocytes and upregulated by glucocorticoid treatment. It has now been found that CD163 is identical to P155 and that this molecule could have activity as an anti-inflammatory molecule. Thus, this glycoprotein is believed to be useful as a biomarker for inflammation and inflammatory conditions and processes in humans.

A method has now been developed for detection of CD163 in human plasma. This method is useful in monitoring inflammation and inflammatory processes in humans.

SUMMARY OF THE INVENTION

An object of the present invention is to provide a method for detecting CD163 in a biological sample, preferably a plasma sample, which comprises contacting the biological sample with a CD163 capture antibody and a CD163 detection antibody, so that levels of CD163 in the biological sample can be quantified. The method of the present invention is particularly useful for monitoring the course of an inflammatory condition or process.

Another object of the present invention is to provide a composition for prevention and treatment of inflammation which comprises CD163. In one embodiment, the composition further comprises a glucocorticoid.

Another object of the present invention is to provide a method for reducing signs and symptoms of inflammation which comprises contacting cells or tissues with the CD163 molecule, either alone or in combination with a glucocorticoid.

Yet another object of the present invention is to provide a method for preventing or treating inflammation in an animal which comprises administering to an animal an effective amount of a composition comprising CD163 either alone or in combination with a glucocorticoid.

DETAILED DESCRIPTION OF THE INVENTION

CD163 is a glucocorticoid inducible member of the scavenger receptor cysteine rich family of proteins. It is known that CD163 is highly expressed on human macrophages but has been reported to be found on less than 50% of peripheral blood monocytes. It has now been found that, contrary to previous reports, more than 99% of all CD14 positive monocytes express CD163. It has also been found that IL-10, like glucocorticoids, induces higher CD163 expression on cultured human monocytes. Glucocorticoid-induced CD163 expression has also been examined and found to be due to an IL-10 independent mechanism since it was not inhibited by anti-IL-10 and was additive with IL-10 treatment. It has also been found that p155, a previously identified monocyte/macrophage marker of unknown function, is the same as CD163. The fact that CD163 is upregulated by potent anti-inflammatory mediators such as glucocorticoids and IL-10 indicates that CD163 may be an important anti-inflammatory molecule and a potential biomarker for inflammation and inflammatory conditions.

Previous studies using mAbs RM3/1, Ber-Mac3 and others had reported that only 0%–40% of circulating monocytes are positive for CD163 (Hogger, P. et al. 1998. *Pharm. Res*. 15:296–302; Hogger et al. 1998. *J. Immunol*. 161:1883–1890; Zwadlo, G. et al. 1987. *Exp. Cell Biol*. 55:295–304; Backe, E. et al. 1991. *J. Clin. Path.*

44:946–953; van den Heuvel, M. et al. 1999. *J. Leuk. Biol.* 66:858–866). However, previous studies with another antibody to p155, a molecule that has been shown to be identical to CD163, Mac 2-48, has consistently demonstrated that virtually all freshly isolated monocytes are positive for CD163. To address the possibility that sub-optimal detection of the lower affinity RM3/1 and Ber-Mac3 antibodies (previously used only with FITC labeled secondary antibodies) might account for this discrepancy, freshly isolated PBMCs were stained with FITC conjugated AML 2.23 (anti-CD14) and biotinylated RM3/1 or biotinylated Mac248, followed by detection with SAPE.

Although Mac2-48 staining was slightly higher, virtually all CD14 bright PBMCs were positive for both RM3/1 and Mac 2-48, while most CD14 dim or negative PBMCs were negative. When PBMCs were gated for CD14 bright cells, greater than 99% were positive for both RM3/1 and Mac 2-48, while the P3 control mAb detected less than 1% of the gated cells. Virtually identical results are obtained when highly purified monocytes were used in place of fresh PBMCS. These results indicate that CD163 is expressed on nearly all CD14-positive circulating monocytes.

To assess whether different cytokines could influence CD163 expression, freshly isolated PBMCs were cultured for 24 hours in the presence of various cytokines, 200 nM DEX (as a positive control for CD163 upregulation), or control media. The cells were then subjected to staining and flow cytometric analysis.

Treatment of PBMCs for 24 hours with IL-10 alone or the synthetic glucocorticoid DEX alone increased monocyte CD163 expression by approximately 4- and 7-fold, respectively ($p<0.01$). Combined DEX plus IL-10 treatment resulted in significantly higher CD163 expression than when monocytes were cultured with DEX only or IL-10 only, indicating an additive effect when glucocorticoid treatment was used in conjunction with IL-10 ($p<0.01$). None of the other cytokines tested had a statistically significant effect on monocyte CD163 expression at the concentrations used, and none significantly increased or decreased the DEX-induced upregulation of expression. The increased expression of CD163 by IL-10 and glucocorticoid treatment was also demonstrated by western blots of monocyte lysates. These data indicated that CD163 upregulation plays an important role in the anti-inflammatory actions of glucocorticoids.

In order to determine whether the increased expression of CD163 on monocytes is due to increased RNA and protein synthesis, northern blots were performed on monocyte lysates. Monocytes were treated for 8 hours with either IL-10, the glucocorticoid FP or control media. CD163 mRNA levels increased from undetectable to strong bands with the addition of IL-10 or FP. This indicated that the induction of CD163 by IL-10 or glucocorticoids is due, at least in part, to increased RNA and protein synthesis.

A dose-response relationship between IL-10 treatment and CD163 expression was established by culturing PBMCs for 24 hours in the presence of 0.1 to 100 ng/ml IL-10. The results were a sigmoidal dose response curve when levels of CD163 expression were related to IL-10 concentration. CD163 expression was increased approximately 3.5 fold by 10 and 100 ng/ml IL-10 treatment when compared to control ($p<0.01$).

It was possible that, in addition to direct effects on mononuclear phagocytes, DEX might upregulate CD163 expression indirectly by altering the amount of IL-10 produced by lymphocytes. In order to test this possibility, PBMCs were cultured with IL-10, DEX or control media in the presence or absence of a blocking anti-IL-10 IgG. Results showed that expression of CD163 was not significantly affected by the presence of anti-IL-10 in control or DEX treated cells. However, IL-10 upregulation of CD163 expression was inhibited by anti-IL-10 ($p<0.01$), where CD163 expression was reduced to near control levels. These findings indicate that DEX increased CD163 expression by an IL-10 independent mechanism.

In addition to testing the effects of cytokines in combination with glucocorticoids on levels of CD163, studies were performed to examine the effects of glucocorticoids in combination with lipopolysaccharide (LPS). Monocytes cultured with LPS alone had low levels of CD163 detected on their surface using an immunofluorescence technique for CD163 detection. Treatment of cells with DEX or IL-10 alone increased expression of CD163, as had been previously shown. However, when monocytes were cultured for 48 hours with DEX combined with LPS, their was a synergistic increase in CD163 expression, where the effect of DEX alone was increased by more than 2-fold when LPS treatment was added.

Additional in vitro studies with LPS showed that LPS induces shedding of monocyte surface CD163 within 2 hours, a result that was consistent with studies by others using the phorbol ester PMA. PMA has been shown to induce rapid shedding of surface CD163 from monocytes in culture, an effect that was blocked by protease inhibitors (Droste, A. Et al. 1999. *Biochem. Biophys. Res. Commun.* 256:110–113). Therefore, like PMA, LPS is capable of inducing CD163 shedding. LPS-induced shedding occurred even with monocytes that had been cultured for 48 hours in DEX and thus had 5- to 10-fold higher levels of surface CD163 than freshly isolated monocytes. In cells that had increased levels of CD163 due to treatment with glucocorticoids plus LPS, as reported above, the surface CD163 molecules are largely resistant to shedding induced by subsequent treatment with LPS, although they remained sensitive to PMA-induced shedding. This LPS-conferred resistance to subsequent LPS-induced shedding of CD163 is similar to reported endotoxin pre-conditioning for resistance to subsequent inflammatory insults.

The effect of the cytokine IL-10 was shown to be unique among the cytokines tested in that, like glucocorticoids, it augmented CD163 expression on freshly isolated mononuclear phagocytes. This increase in CD163 is thought to be a direct effect on monocytes, as studies using highly purified monocytes or the established human monocyte cell line THP-1 yielded results that were in agreement with those performed using PBMCs. In contrast, a number of other cytokines (including IL-4 and IL-13) did not upregulate CD163 expression at the concentrations tested. Even though IL-4, IL-10 and IL-13 have all been reported to inhibit monocyte production of inflammatory cytokines such as TNFA (Cosentino, G. et al. 1995. *J. Immuno.* 155:3145–3151; Joyce, D. A. et al. 1996. *Cytokine* 8:49–57; Joyce, D. A. et al. 1996. *J. Interferon Cytokine Res.* 16:511–517), differential regulation of mononuclear phagocyte surface molecules by IL-10 and IL-4/IL-13 is not without precedent. For example, CD64, like CD163, is upregulated by IL-10, but not by IL-4 or IL-13 (de Waal Malefyt, R. et al. 1993. *J. Immunol.* 151:6370–6381; te Velde, A.A. et al. 1992. *J. Immunol.* 149:4048–4052).

When given in combination with DEX, IL-10 is the only cytokine tested that significantly increased CD163 expression over DEX treatment alone. Since the concentration of DEX used is >90% saturating for the glucocorticoid receptor and the dose of IL-10 used gives maximal CD163 induction, the additive effect of these treatments suggests that glucocorticoids and IL-10 influence CD163 expression by independent mechanisms. This conclusion is further supported by the finding that an anti-IL-10 antibody (which blocks the biological activity of IL-10) reduced the IL-10 induction of CD163 to control levels, but had no effect on the DEX induction of CD163. This demonstrates that the glucocorticoid effect is not dependent on elevated levels of extracellular IL-10 and does not upregulate CD163 expression by first increasing IL-10 synthesis and release.

The finding that either GM-CSF or IL-4 plus DEX does not enhance CD163 expression over DEX treatment alone contrasts with that of a recent report. While Van den Heuvel and colleagues (van den Heuvel, M. et al. 1999. *J. Leuk. Biol.* 66:858–866) found that neither GM-CSF nor IL-4 alone had any effect on CD163 expression, they detected a synergistic effect using either GM-CSF or IL-4 plus DEX. This disparity is likely due to differences in experimental procedures such as isolation technique, culture conditions and duration of stimulus. In the previous report, monocytes were purified by gradient centrifugation, lymphocyte resetting and monocyte adherence while the present studies used density centrifugation purified PBMCs. Furthermore, cells were treated for 24 hours, while in the previous study cells were treated for 2 days.

The dose response curve for the IL-10 effect on CD163 expression demonstrates a dynamic range of IL-10 concentrations that is from 0.1 ng/ml to 10 ng/ml. This is consistent with previous findings concerning the effect of IL-10 on a wide range of monocyte functions such as tissue factor expression and associated procoagulant activity (Ernofsson, M. et al. 1996. *Br. J. Haematol.* 95:249–257; Ones, L. T. et al. 1996. *Cytokine* 8:822–827), as well as MIP-1α (Berkman, N. et al. 1995. *J. Immunol.* 155:4412–4418), metalloproteinase (Lacraz, S. et al. 1992. *J. Clin. Invest.* 90:382–388) and TNF receptor (Hart, P. H. et al. 1996. *J. Immunol.* 157:3672–3680) expression.

The fact that CD163 is upregulated by potent anti-inflammatory mediators such as glucocorticoids and IL-10 indicates that this CD163 may be an important anti-inflammatory molecule. Further, these data provide support for the use of CD163 detection in biological samples, such as blood or plasma, as a means for detecting the presence of inflammation or inflammatory conditions in patients.

In order to provide for use of CD163 as a biomarker of inflammation, a method for detection of CD163 in biological samples such as plasma was developed. The assay of detection is an ELISA assay using a CD163-specific antibody such as MAC2-158 or MAC2-48 as the CD163 capture antibody and the commercially available biotinylated antibody RM3/1 as the CD163 detection antibody. Briefly, plates were coated with purified MAC2-158 or MAC2-48 antibody and incubated overnight at 4 C. After washing, non-specific binding was blocked by adding blocking buffer to each plate well and incubating for 30 minutes at room temperature. After washing, plasma samples to be tested were added and the plates are incubated overnight at 4 C or at room temperature for 2 hours. After washing, the detection antibody was added, RM3/1, and the plates agin incubated. A streptavidin alkaline phosphatase tag was used and the plates were developed.

Using this assay, relative levels of CD163 were assayed in the plasma of 4 patients undergoing cardiac surgery performed with normothermic cardiopulmonary bypass. It is known that cardiac surgical patients exhibit a reproducible acute, inflammatory response as indicated by a rise in TNF, IL-6 and cortisol, followed by hepatic release of acute phase proteins. This response may be caused by several mechanisms, including tissue trauma, ischemia-reperfusion injury, exposure to foreign membranes (when cardiopulmonary bypass is used) and transient endotoxemia. In 4 of 4 samples from these patients that were tested, plasma CD163 increased approximately twofold at 60 minutes following cardiopulmonary bypass, and returning to slightly below baseline levels on post-operative day 1. In addition, levels of CD163 in plasma of these patients was shown to correlate with levels of interleukin-6 (IL-6) in plasma. This is an important finding because prior to surgical stress, infection, or other inflammatory processes, there is no detectable IL-6 in plasma of humans. Therefore, these data demonstrate the link of CD163 time-course with other markers of inflammation and provide the first demonstration that soluble CD163 acts as an acute phase protein during an inflammatory response.

In order to more closely mimic the in vivo inflammatory response to infection in a more controlled setting than the cardiac patients described above, healthy volunteers were administered a 4 ng/kg bolus infusion of LPS and monitored the levels of soluble CD163 in plasma. As described above, LPS had been shown to induce shedding of CD163 from monocytes in vitro. Plasma samples were taken at baseline (before administration of LPS), and then at various time points after LPS infusion up to 72 hours after infusion initiation. Levels of CD163 in plasma were measured using the assay of the present invention. Soluble CD163 levels in plasma increased as much as 7-fold compared to baseline levels, peaked at 1 to 2 hours, and remained elevated in 4 of 5 volunteers at 12 hours post LPS administration. In the one volunteer where levels had declined at 12 hours, levels remained elevated up to 4 hours before returning to baseline levels by 8 hours. Changes in levels of known acute phase proteins, glucocorticoids, and pro- and anti-inflammatory cytokines were also monitored in order to determine if their levels correlated with the appearance of soluble CD163 in plasma. Levels of CRP, an acute phase plasma protein secreted in hepatocytes in response to an inflammatory stimulus, increased in plasma by 8 hours but did not peak until 24 hours post LPS administration. Plasma levels of TNFA, IL-6 and IL-10, all known to be produced following LPS infusion, peaked at 1, 2, and 4 hours post LPS administration, respectively. Plasma cortisol levels began to increase at 4 hours post LPS administration but did not peak until 6 hours. Theses data demonstrated that soluble CD163 is one of the earliest changes induced by an acute inflammatory response that can be detected in plasma. Therefore, CD163 acts as an early signaling event in the inflammatory response cascade.

Accordingly, the present invention provides a method for detecting levels of CD163 in biological samples from individuals known to have or suspected of having inflammation or inflammatory conditions. By biological samples it is meant to include, but is not limited to, plasma, whole blood, serum, urine, sputum, semen, cerebrospinal fluid, or synovial fluid. The inflammatory condition can be due to variety of causes including, but not limited to, lupus, rheumatoid arthritis, infection, and surgery. The method involves contact of a biological sample, such as plasma, with a CD163-specific antibody such as MAC2-158 or MAC2-48, and then detection in the ELISA assay with a biotinylated antibody such as RM3/1. This method is particularly useful in monitoring for the presence or course of inflammation or inflammatory conditions in a patient.

The present invention also relates to compositions comprising CD163 for use in the prevention and treatment of inflammation in animals, including humans. In one embodiment of the invention, cells or tissues are contacted with CD163 and inflammation is prevented, suppressed or reversed. In another embodiment, a composition comprising CD163 in a pharmaceutically acceptable vehicle is administered to an animal suffering from inflammation or an inflammatory disease so that the inflammation or inflammatory disease is treated. Successful treatment is indicated by a reduction in the signs and symptoms of inflammation including a reduction in the presence of inflammatory mediators, such as cytokines. CD163 can be administered alone or in combination with another anti-inflammatory agent such as a glucocorticoid. In the context of the present invention, "effective amount" is an amount of CD163 capable of producing a desired pharmacological effect such as a reduction in the signs and symptoms of inflammation. Selection of additional anti-inflammatory agents to be administered in conjunction with CD163 can be performed routinely by one of skill in the art. Selection of the amount of CD163 to be administered can also be performed routinely by one of skill based upon results such as the cell culture studies presented herein.

The following non-limiting examples are provided to better illustrate the present invention.

EXAMPLES

Example 1

Isolation and Culture of Peripheral Blood Mononuclear Cells (PBMCs)

PBMCs were isolated from heparinized human whole venous blood using Ficoll-Hypaque (d=1.077g) after the method of Böyum (Boyum, A. 1968. *Scand. J. Clin. Lab. Invest. Suppl.* 97:77–89). PBMCS were then washed three times with hepes buffered RPMI 1640 (Hazelton Biologicals, Lenexa, Kans.)/0.05% gentamicin (Elkins-Sinn, Inc., Cherry Hill, N.J.)/1% fetal bovine serum (FBS) (Hyclone Laboratories, Inc., Logan, Utah).

For cytokine treatment studies, isolated PBMCs were suspended in hepes buffered RPMI 1640/0.05% gentamicin/ 10% FBS at a concentration of $2.0 \times 10^6$ to $2.5 \times 10^6$ cells/ml and cultured in 96 well plates at 37° C. and 5% $CO_2$ in the presence of various mediators (Table 1). Mononuclear cells were stained for flow cytometric analysis after 24 hours in culture unless otherwise indicated. This enhanced cell recovery because monocytes, which initially adhere to plastic vessels, transiently detach from culture wells at 24–48 hours.

Example 2

Staining and Flow Cytometric Analysis

All staining procedures were performed at 4 C. Briefly, cultured PBMCs were incubated with normal human IgG (6 mg/ml) to block Fc receptor-specific binding of mAbs and 30 µg/ml of the isotype control mAb P3 or a saturating amount of mAb MAC2-48 (20 µg/ml) for one hour. Cells were then washed and stained for one hour with 17.5 µg/ml FITC labeled goat F(ab=)$_2$ anti-mouse Ig. The cells were again washed and fixed with 1% methanol free formalin.

For two color studies, cells were stained for one hour with 20 µg/ml biotinylated MAC2-8, RM3/1, or P3 plus 20 µg/ml FITC AML 2.23 or FITC control mouse mAb in the presence of at least 2 mg/ml normal human IgG in a total volume of 60 ml. After staining with primary mAbs, cells were washed and stained with SAPE at a 1:40 dilution. Flow cytometric analysis was performed on washed, unfixed cells soon after staining.

Cell fluorescence of monocytes gated using forward and side scatter was analyzed using a Becton Dickenson FACScan (Franklin Lakes, N.J.). Mean fluorescence intensity (MFI) was calculated by subtracting the MFI of the P3 stained mononuclear cells from the MFI of the corresponding Mac 2-48 stained cells.

Example 3

Northern Hybridization

Human monocytes were isolated and cultured overnight as described for western blots. Monocytes were then stimulated for 8 hours with 5 ng/ml IL-10 (R&D Systems) or $10^{-8}$ M FP. Total RNA was isolated from IL-10 stimulated, glucocorticoid stimulated and control monocytes as described by Dreier, et al. (Dreier, J. et al. 1998. *DNA Cell Biol.* 17:321–323). 10 µg of total RNA per sample were electrophoretically separated in a 1% agarose, 2% formaldehyde gel and transferred onto a Hybond N$^+$ nylon membrane (Amersham Inc., Arlington Heights, IL) in 20× saline-sodium citrate (SSC) using an LKB 2016 VacuGene blotting apparatus. Antisense RNA probes for northern hybridization were generated from linearized DNA templates using a digoxigenin RNA labeling kit (Boehringer Mannheim, Mannheim, Germany) and T7 RNA polymerase (New England Biolabs, Schwalbach, Germany) as described by the manufacturer. Prehybridization was performed at 68° C. for 1 hr in a high SDS hybridization buffer (7% SDS, 5×SSC, 50% formamide, 50 mM sodium phosphate, 2% casein, 0.1% N-lauroylsarcosine, pH 7.0). Subsequently the heat-denatured probes (10 minutes at 95° C.) were added to the pre-hybridization solution (100 ng/ml) and hybridized at 68° C. for 16 hours. The nylon membrane was washed twice for 5 minutes at room temperature in a 2×SSC, 0.1% SDS solution and twice for 15 minutes at 68° C. in 0.5×SSC and 0.1% SDS. The hybridization results were visualized by chemiluminescent detection with anti-digoxigenin Fab=fragments conjugated with alkaline phosphatase and substrate CSPD as described by the manufacturer (Boehringer Mannheim). Equal loading of samples was examined by hybridization of RNA with an actin antisense RNA probe.

Example 4

ELISA Assay for CD163

ELISA plates were coated, 100 µl per well, with 5 µg/ml purified MAC2-158 (coating buffer of 0.1 M NaHCO$_3$ 0.5 M NaCl, adjusted to pH 8.4 with HCl). Plates were incubated overnight at 4 C. and then washed 4 times with wash buffer (1× phosphate buffered saline and 0.05% Tween 20). Nonspecific binding was blocked by adding 200 µl blocking buffer to each well (phosphate buffered saline with 10% FBS) and incubating the plates for 30 minutes at room temperature. Plates were then washed 3 times with wash buffer. 100 µl plasma (1:10 dilution) was added and the plates incubated overnight at 4 C., or for 2 hours at room temperature. Each plate was washed 4 times with wash buffer. The detection antibody RM3/1 was added in blocking buffer (100 µl; phosphate buffered saline+10% FBS)) and the plates were incubated for 1 hour followed by washing 4 times with wash buffer. Streptavidin alkaline phosphatase (1/1000) was added in blocking buffer and the plates were incubated for 30 minutes at room temperature, followed by 4 washes with wash buffer. The reaction was developed with a PNPP system by dissolving one 15 mg PNPP tablet (Sigma Chemical Co.) in 15 ml PNPP diluent (0.05 M $Na_2CO_3$, 0.001 M $MgCl_2$, pH 9.75) and adding 100 μl of solution to each well. Plates were developed for 5 to 30 minutes. 100 μl 1 M NaOH was added to stop the reaction. The plates were read on a spectrophotometer at 405 nM.

What is claimed is:

1. A method for detecting the presence of soluble CD163 that is shed into plasma in vivo, in a biological sample comprising:
   a) contacting a biological sample with a CD163 capture antibody to form a soluble CD163-capture antibody complex;
   b) contacting the soluble CD163-capture antibody complex with a CD163 detection antibody so that the CD163 detection antibody binds to the soluble CD163-capture antibody complex; and
   c) detecting the presence of the CD163 detection antibody that bound to the soluble CD163-capture antibody complex, thereby detecting the presence of soluble CD163 in the sample wherein the biological sample is human plasma.

2. The method of claim 1 wherein the CD163 capture antibody is MAC2-158 or MAC2-48 and the CD163 detection antibody is RM3/1.

* * * * *